United States Patent
Sarrine et al.

[19]

[11] Patent Number: 6,068,753
[45] Date of Patent: May 30, 2000

[54] AUTOMATIC ELECTROPHORESIS APPARATUS WITH FLUORESCENT AND VISIBLE SCANNING

[75] Inventors: Robert J. Sarrine, Beaumont; Charles D. Kelley, Lumberton; Henry A. Garsee, Kountze; Tipton L. Golias, Beaumont, all of Tex.

[73] Assignee: Helena Laboratories Corporation, Beaumont, Tex.

[21] Appl. No.: 08/847,226

[22] Filed: May 1, 1997

Related U.S. Application Data

[60] Provisional application No. 60/016,951, May 6, 1996.

[51] Int. Cl.⁷ .............................. G01N 21/64; G01N 27/26
[52] U.S. Cl. ...................... 204/612; 204/606; 204/608; 204/618; 204/621; 356/344
[58] Field of Search .................... 204/606, 608, 204/612, 613, 618, 621, 456, 461; 356/344

[56] References Cited

U.S. PATENT DOCUMENTS

| | | | |
|---|---|---|---|
| 4,130,824 | 12/1978 | Amos et al. | 356/344 |
| 4,360,418 | 11/1982 | Golias | 204/613 |
| 4,391,689 | 7/1983 | Golias | 204/613 |
| 4,571,149 | 2/1986 | Soroka et al. | 414/750 |
| 4,572,671 | 2/1986 | Kaneko | 204/612 |
| 4,684,244 | 8/1987 | Butts et al. | 356/39 |
| 4,909,920 | 3/1990 | Sarrine et al. | 204/608 |
| 4,954,237 | 9/1990 | Sarrine et al. | 204/608 |
| 4,960,999 | 10/1990 | McKean et al. | 250/461.1 |
| 4,986,891 | 1/1991 | Sarrine et al. | 204/608 |
| 5,104,512 | 4/1992 | Gombocz et al. | 204/616 |
| 5,120,419 | 6/1992 | Papp | 204/612 |
| 5,147,522 | 9/1992 | Sarrine et al. | 204/608 |
| 5,459,325 | 10/1995 | Hueton et al. | 356/317 |
| 5,460,709 | 10/1995 | Sarrine et al. | 204/612 |
| 5,478,184 | 12/1995 | Bryant et al. | 414/331 |
| 5,528,050 | 6/1996 | Miller et al. | 250/585 |
| 5,578,818 | 11/1996 | Kain et al. | 250/234 |
| 5,774,214 | 6/1998 | Prettyjohns | 204/612 |
| 5,888,825 | 3/1999 | Carr et al. | 436/48 |

Primary Examiner—Robert Warden
Assistant Examiner—Theresa T. Snider
Attorney, Agent, or Firm—Dorsey & Whitney LLP

[57] ABSTRACT

An apparatus for electrophoresing a sample and for thereafter either scanning in the visible mode or the fluorescent mode, under control of a central processor, to provide scanning densitometry of the electrophoresed sample, and with the fluorescent mode scanning being performed in situ. The apparatus includes a gantry which moves from left to right in the XY plane. The gantry draws, delivers and deposits the samples and reagents, and includes safety devices to prevent the gantry from movement and damage when there are obstructions in the path of the gantry. A fluorescent scanning unit is moved by X- and Y-direction motors to position a photomultiplier over an electrophoresed sample. In this way, the electrophoretic sample can remain fixed in place during sample delivery, ultraviolet exposure and measurement operations.

17 Claims, 17 Drawing Sheets

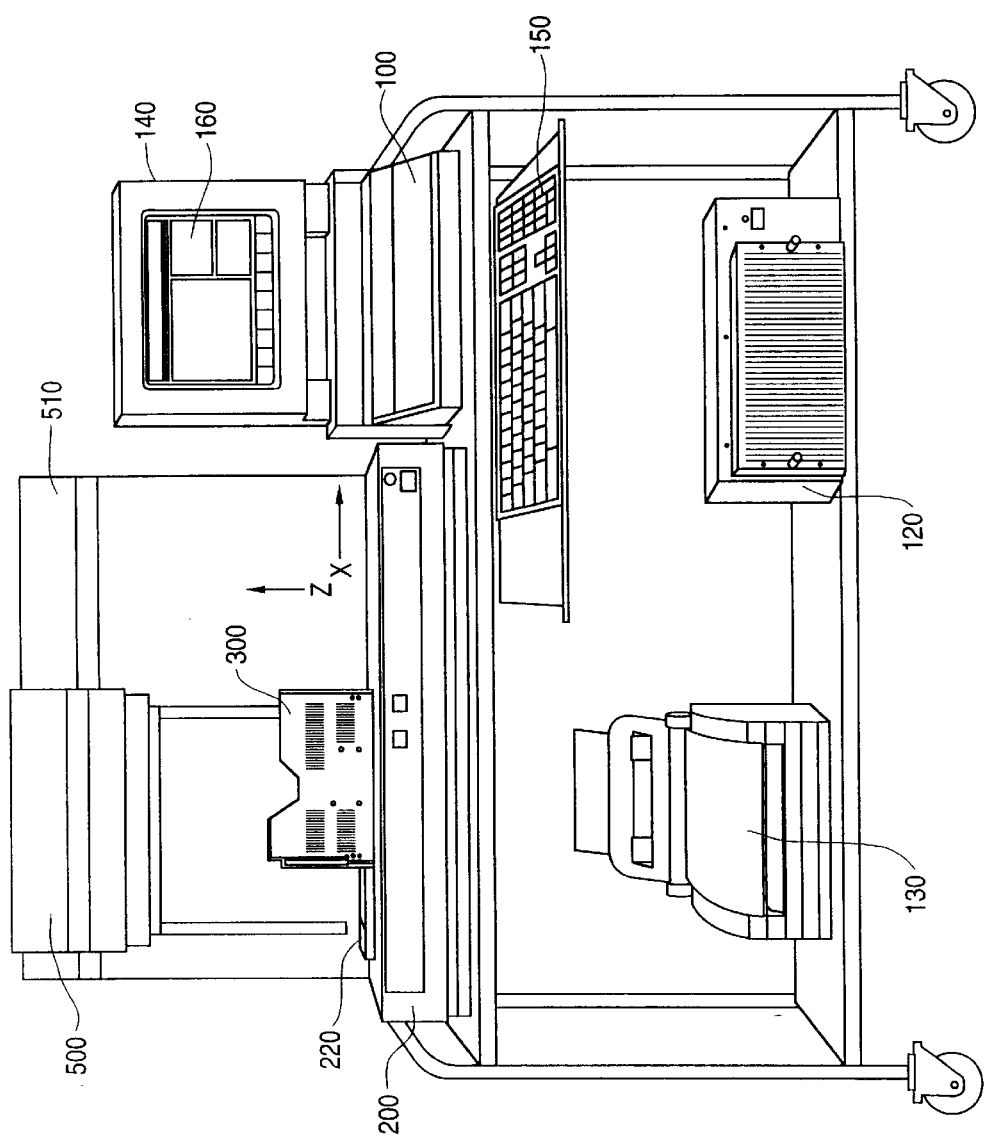

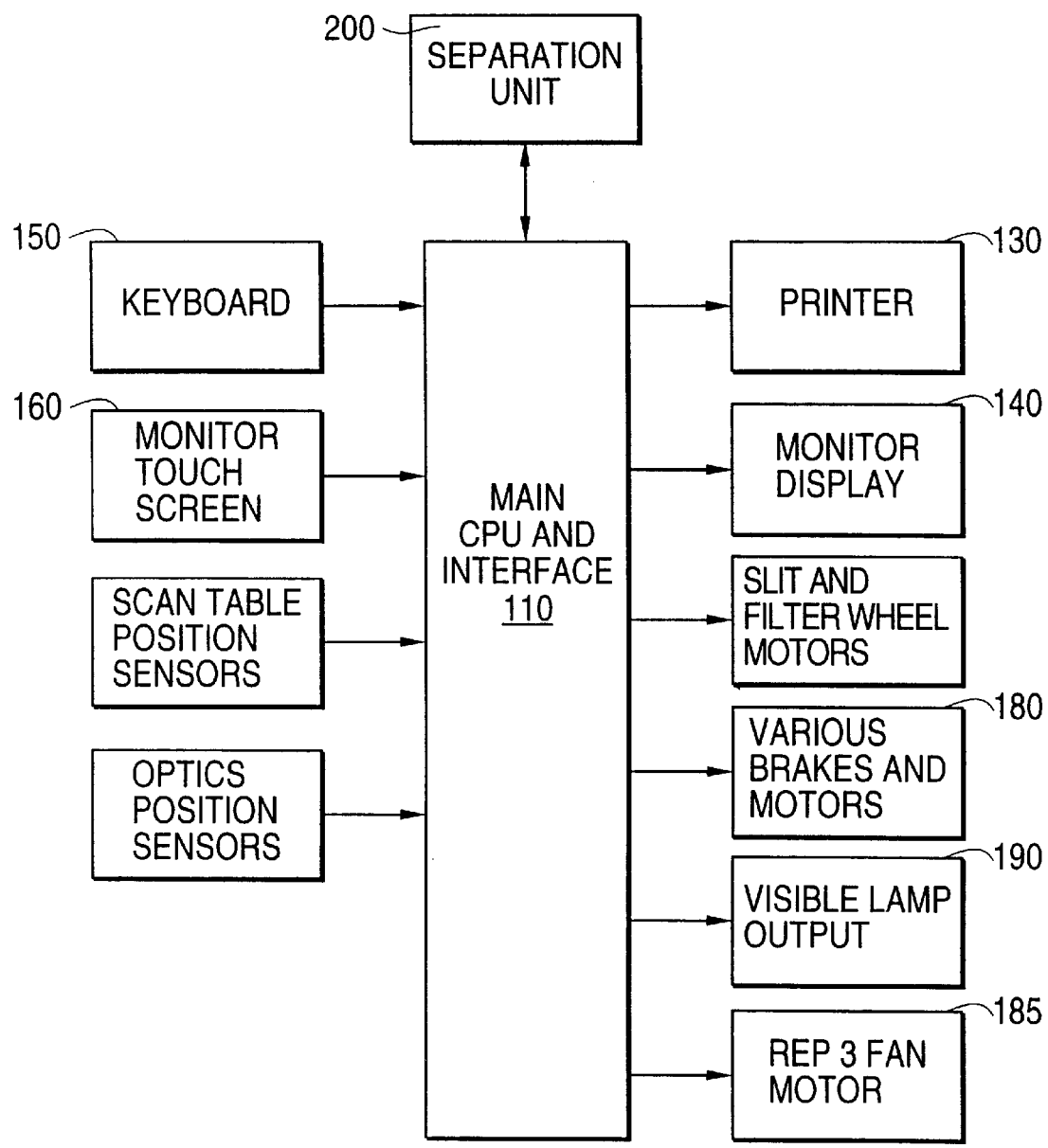

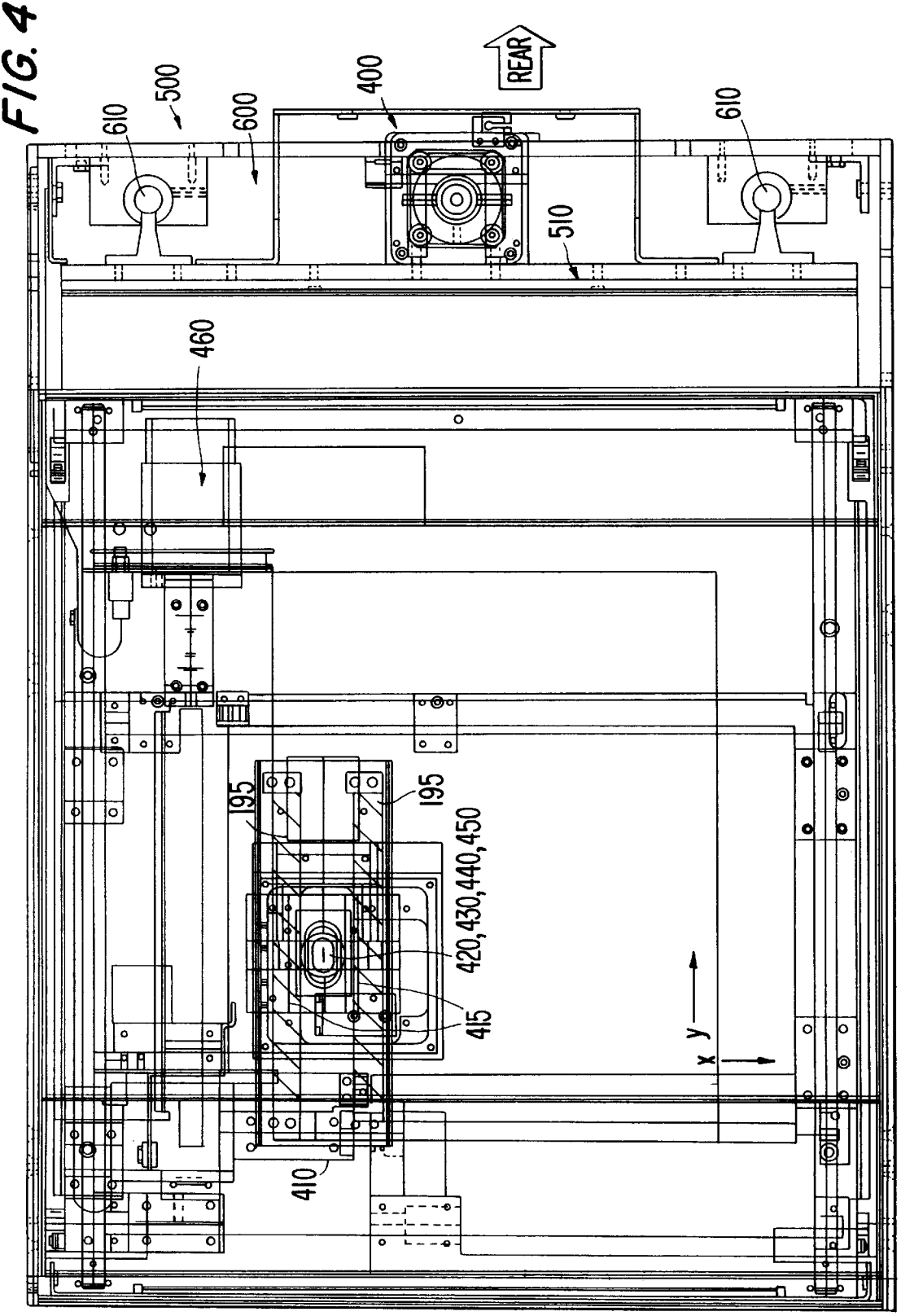

AUTOMATIC ELECTROPHORESIS APPARATUS WITH FLUORESCENT AND VISIBLE SCANNING

CROSS-REFERENCE TO RELATED APPLICATIONS:

This application is based on provisional application 60/016,951 filed May 6, 1996, which is hereby incorporated herein by reference. The documents identified in the provisional application as "Related Applications" and the documents filed with the provisional application as "Appendices A through E" are incorporated herein by reference. All patents and patent applications and publications identified in the specification of the provisional application are incorporated herein by reference.

BACKGROUND OF THE INVENTION

1. Field of the Invention

This invention is related in general to the field of electrophoretic analysis of liquid samples. In particular, the invention relates to an apparatus and method for the electrophoresis process beginning with the step of applying liquid samples to an electrophoresis support media and, without moving the support media, further including the steps of electrophoresing, staining, incubating, and drying the sample. The present invention further includes the scanning and densitometry measurements on the scanned samples in both the visible and fluorescent modes.

Electrophoresis is the science of moving charged particles in an electric field through a solid or semi-solid media. The technique is most commonly used in medical research in medical laboratories for analyzing various blood proteins.

2. Description of the Prior Art

In the diagnoses of ailments of human beings and animals, it is known that much information can be provided by an analysis of specific biological fluids such as blood serum proteins, lipoproteins, hemoglobin, and isoenzymes. It is well known that electrophoresis is an effective method of separating the respective components of such fluids for analysis or for employing optical densitometry techniques in analyzing the samples.

In the basic method of electrophoresis, charged molecules of the sample fluids are separated under the influence of an electrical field wherein the liquid sample to be examined is applied to a support medium having a porous surface. Because the various components of the fluid move at different rates through the support medium, the liquid sample may be separated into its respective components. Subsequent staining of the fractional components in the support medium may then be subjected to optical densitometry or other methods for examination.

The electrophoresis process has been performed through a series of manual steps for many years. The manual process typically has started with the laboratory technician preparing an electrophoresis chamber by filling appropriate cavities of the chamber with buffer solution. Buffer solution is a liquid used in the electrophoresis process to maintain the support medium surface in a moist condition and to provide an electrical interface to a power source applied to the chamber so that an electric field may be applied to the support medium. The support medium is typically a piece of MYLAR™ backing which has been coated with a gel substance such as cellulose acetate or agarose. The liquid sample to be examined is typically a blood serum, but of course may be other liquids, the components of which may be moved through an electric field.

After the laboratory technician has prepared the electrophoresis chamber, the laboratory technician applies as precisely as possible, consistent volumes of the samples to precise locations on the support medium. The laboratory technician then places the support medium into the electrophoresis chamber so that the edges of the support medium are immersed in two buffer cavities at each of its longitudinal ends. Electrophoresis is then performed using a precise and consistent high voltage applied for a precise and consistent interval of time across the buffer cavities.

After electrophoresis has been completed, the laboratory technician applies a uniform coating of staining reagent or stain to the surface of the support medium allowing a precise and consistent interval of time for the reagent and sample to chemically combine. The staining reagent is a liquid used after electrophoresis to chemically combine with the separated components of the fluid sample, causing its components to exhibit optical characteristics.

Next, the laboratory technician incubates the support medium using a precise and consistent temperature and time interval. Incubation is the process of controlling the chemical reaction between the components of the liquid sample and the staining reagent by means of applying heat for a fixed interval of time.

Next, the laboratory technician dries the sample plate by increasing the temperature for a second precise and consistent temperature and time interval. The drying process stops the reaction between the sample plate and the reagent by removing water from the support medium.

One of the problems associated with the manual support medium preparation relates to the difficulty of precise application of the liquid samples to the support medium which is to be subjected to electrophoresis. The samples may be applied to the support medium one at a time in serial fashion with a hand pipettor, but the hand pipettor must be rinsed with a cleansing agent and blotted before a new sample is aspirated and then applied to the strip. Applicators have been designed to apply fluid samples simultaneously or in "parallel" to the strips. Such applicators are described at page 61 of the General Products Catalog for 1984–1985 of Helena Laboratories of Beaumont, Tex. Such applicators may apply eight, twelve or more samples to a microporous support medium and have the advantage of making the electrophoresis technique easier and more reproducible.

There have been prior art apparatus and method available for automatically performing electrophoresis and staining of the plurality of samples applied to a support medium. For example, U.S. Pat. No. 4,360,418 to Golias and U.S. Pat No. 4,391,689 to Golias describe an automated electrophoresis and staining apparatus and method.

Such apparatus includes an electrophoresis chamber and a series of vats mounted upon a platform and arranged in a row where the vats are adapted to contain respectively a liquid stain and a series of plate processing solutions. A plate holder rack, having a horizontal open frame, supports an upright electrophoresis plate or support medium onto which a sample for electrophoretic fractionization has been applied. Such electrophoresis plates required the initial preparation by application of liquid samples either manually or by using one of the parallel applicators described above. The plate is nested within a chamber which includes an electrophoretic circuit and the samples are electrophoresed for a predetermined time period. A power operated lift and transfer assembly is provided to lift, transfer and lower the plate holder rack and plate from the chamber progressively into each of the underlying vats for a predetermined period in a linear stepping motion while maintaining the plate in an upright position at all times. It is noted that the staining process relies on chemical procedures for the staining process rather than the manual system described above where incubation and drying are used. Although the apparatus described above has many desirable features, it has a practical disadvantageous feature in that it requires providing a plurality of chemicals and wash solutions in the unit which must be maintained periodically.

Prior art apparatus and methods for optically scanning support media which have been subjected to electrophoresis and staining have used devices such as photomultipler tubes, photodiodes or similar devices which produce an electric current or voltage output proportional to the light falling on such device. These devices are generally referred to as detectors. Prior art instruments employing these detectors are used for determining various physical properties of the samples which have been prepared by electrophoresis. The properties of interest concerning the separated bands of the sample are size and optical density or intensity of emitted light which is of a wave length different from that of the excitation light source. Separated bands of each sample which have been subjected to electrophoresis are known components of the sample under test and it is desirous that they be quantified for the purpose of aiding in medical diagnosis or research.

The known instruments which use the detectors referred to above generally find it necessary to use a blocking optical slit. The purpose of the slit is to allow the detector to "instantaneously view" a portion of the sample plate which is the same relative size and shape as the slit. The detector then produces an electrical current or voltage which is proportional in amplitude to the magnitude of the light detected. The current or voltage produced is then converted by means of an analog to digital converter and the resultant digital representation of the light magnitude is stored in an organized format in a digital computer memory.

It is an object of the present invention to provide automatic electrophoresis through the drying step, i.e., all the steps being performed without laboratory technician intervention.

It is an object of the present invention to provide automatic electrophoresis with fluorescent scanning, i.e., all the steps through and including the fluorescent scanning being performed without laboratory technician intervention.

It is an object of the present invention to provide an electrophoresis system with both visual and fluorescent scanning modes.

It is an object of the present invention to provide in-situ fluorescent scanning.

It is an object of the present invention to automatically deposit a sample in any location or configuration on the electrophoresis plate.

It is an object of the present invention to vary the quantity of the sample drawn from a sample supply and delivered to the electrophoresis plate.

It is an object of the present invention to aspirate and to deposit the sample from various position along the Z-axis (vertical).

It is an object of the present invention to control temperature within an electrophoresis chamber.

It is an object of the present invention to provide a thermoelectric heating/cooling device in the bottom of the electrophoresis chamber for cooling the electrophoresis plate.

It is an object of the present invention to provide additional electrodes to create a plurality of electrical zones within the electrophoresis chamber.

It is an object of the present invention to provide automatic electrophoresis with fluorescence with self-calibration.

It is an object of the present invention to automatically edit the graphic results obtained by scanning the electrophoresed sample to exclude aberrational data, including noise and artifacts.

SUMMARY OF THE INVENTION

The present invention provides an automatic electrophoresis apparatus with fluorescent scanning. The present invention allows the laboratory technician to perform automatic electrophoresis with fluorescent scanning by entering data into a computer, e.g., the type of sample and test to be performed, manually depositing a large quantity of the sample and reagent in appropriate trays, and inserting the proper electrophoresis plate. This is a considerable improvement over the prior art because electrophoresis is labor intensive and, until now, there was no automated electrophoresis apparatus with fluorescent scanning. Further, until the present invention, there was no electrophoresis system which provided both visual and fluorescent scanning modes. Further, in the preferred embodiment the fluorescent scanning is performed in situ, i.e., with no laboratory technician movement of the gel electrophoresis plate during either the electrophoresis or scanning operations.

The present invention includes numerous improvements on the existing automated apparatuses and dramatically increases the opportunity for the laboratory technician to create a variety of tests and configurations. First, the present invention performs in-situ fluorescent scanning. Second, the present invention provides for depositing the sample for various thickness electrophoresis plates depending on the sample, test, and thickness of the electrophoresis plate. Third, the present invention can deposit the sample in any location on the electrophoresis plate, not just one or two fixed positions as in the prior art. Fourth, since the process of electrophoresis is temperature sensitive, the present invention includes a thermoelectric heating/cooling device for controlling the temperature of the electrophoresis plate. Cooling the electrophoresis plate has also proven to improve fluorescent activity. Fifth, the present invention provides for a varying the size or amount of sample drawn from the sample tray and the amount deposited on the electrophoresis plate, as contrasted to prior systems which permitted only a fixed quantity of sample to be deposited. Sixth, the present invention provides for the creation of additional electrophoresis or separation zones in the electrophoresis chamber.

The present invention offers considerable improvements with regard to safety including microswitches at the bottom of the cover of a fluorescent scanner to prevent closing the apparatus on the hand of the laboratory technician. The present invention includes a gantry which draws, delivers and deposits the samples and reagents, and includes safety devices to prevent the gantry from movement and damage when there are obstructions in the path of the gantry. Thus the present invention offers considerable improvements over the prior art with regard to functionality, performance, and safety.

BRIEF DESCRIPTION OF THE DRAWINGS

FIG. 1B is a perspective view of the components of the preferred embodiment on a mobile cart.

FIG. 2 is a block diagram of the central processing unit (CPU) located in the visible scanner.

FIG. 4 is a top view of the fluorescent scanner.

DESCRIPTION OF THE PREFERRED EMBODIMENT

Figure 1A:
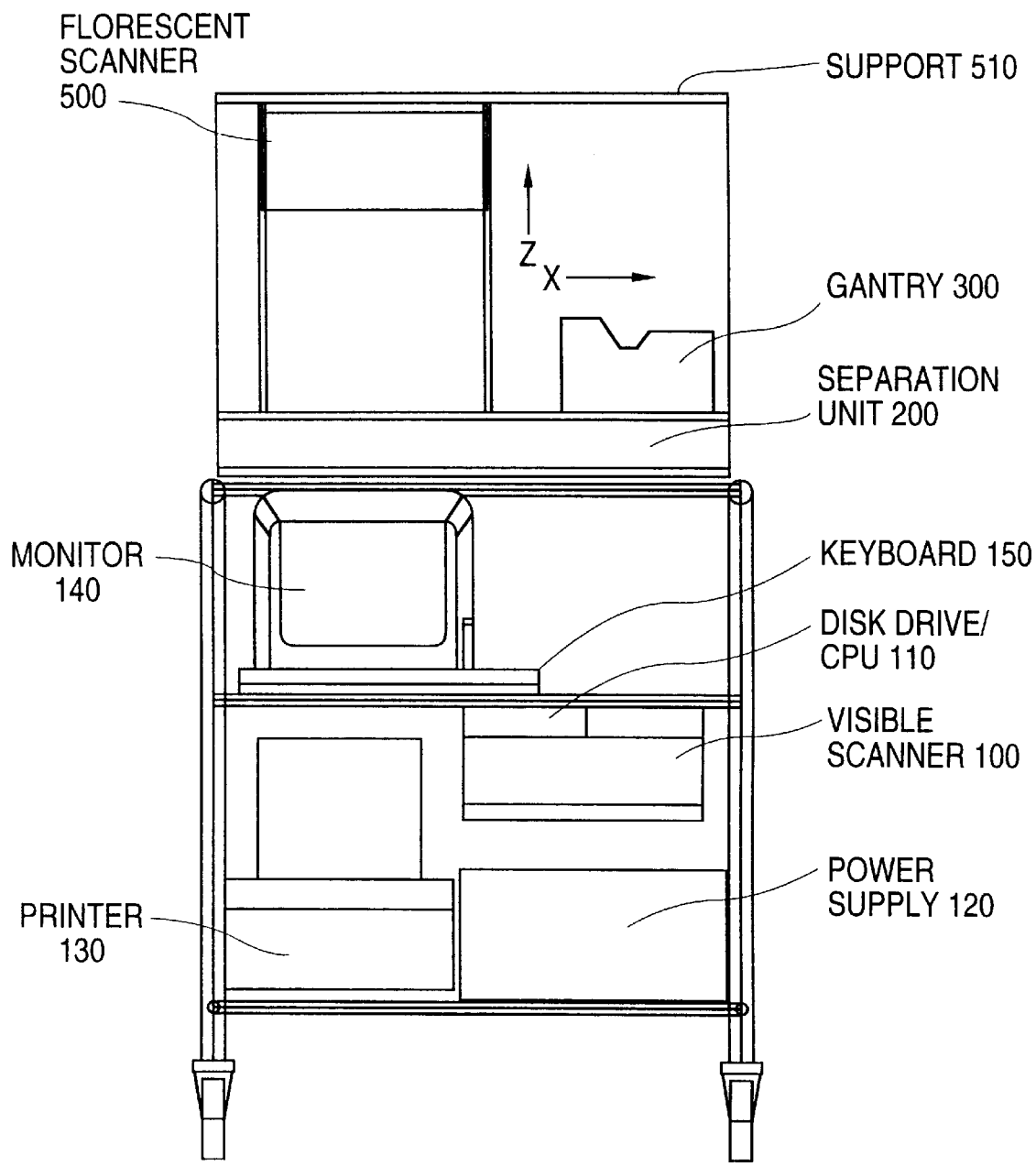
FIG. 1A is a diagram of the components of the preferred embodiment on a mobile cart.

FIGS. 1A and 1B shows the preferred embodiment for the automated electrophoresis apparatus with a fluorescent scanner 500. The method and apparatus automate or eliminate the technique-dependent steps of conventional electrophoresis and scanning. The present invention performs scanning in both the fluorescent and visual modes. The present invention performs in-situ electrophoresis and fluorescent scanning. In this preferred embodiment, the apparatus contains a fluorescent scanner 500, a separate visual, or visible, scanner 100, a keyboard 150, a gantry 300, a separation unit 200, a monitor 140, a central processing unit (CPU) 110, a printer 130, and a power supply 120.

Figure 5A:
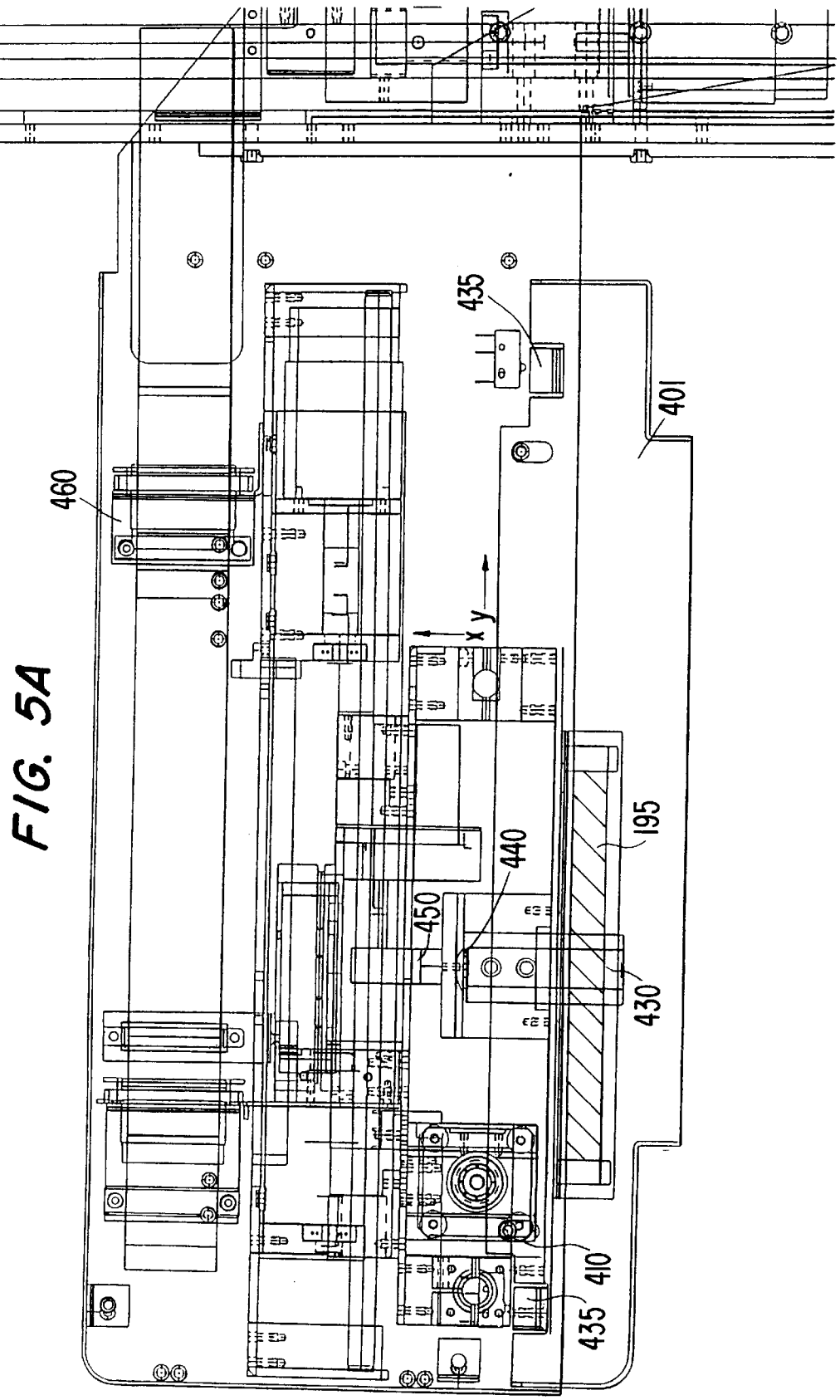
FIG. 5A is a side view of the fluorescent scanner.

As shown in FIGS. 4 and 5A, the fluorescent scanner 500 includes a fluorescent scanning unit 415 including an ultraviolet light source 195, a collimator 430, an ultra-violet light filter 440, and a photomultiplier tube 450. The scanning unit 415 is moved in the X and Y directions by operation of stepper motors 410, and 460, respectively. Motorized mechanics 400 move the fluorescent scanner 500 along the Z-axis, which is the conventional nomenclature. During fluorescent scanning, the ultraviolet light source 195 radiates an electrophoresis plate 220 and sample (not shown in FIGS. 4 and 5A). The collimator 430 receives light emitted from the sample and emits a parallel beam of radiation. The ultraviolet filter 440 then filters out certain wavelengths of light which was collimated by the collimator 430 and then the photomultiplier tube 450 receives the emitted light to be measured. The fluorescent scanner 500 moves down onto the separation unit 200 for scanning or away from the separation unit 200 to provide physical clearance for movement of the gantry 300 (see FIG. 1A).

In the fluorescent scanning mode, the CPU 110 controls the position of the fluorescent scanner 500 with greater precision than in the prior art through the use of encoders in combination with stepper motors and home switches to continuously track the exact location of the flourescent scanner 500. This is especially important because the present invention is capable of performing a plurality of different tests, which may require the flourescent scanner 500 to be in different positions.

Thus according to the present invention, the flourescent scanner 500 may be positioned at any location along the Z-axis and the fluorescent scanning unit 415 may be positioned at any location along the X-axis and the Y-axis. This allows a sample to be placed at any location in the X, Y and Z directions. The Z direction, as shown in FIGS. 1A and 1B, runs from the bottom to the top of the system and the X direction is "left to right" as viewed from the front of the system. The "Y" direction is "forward to rearward". These are conventional nomenclatures. Thus the present invention permits scanning throughout the X and Y directions with application of the sample at various heights, i.e., in the Z-direction. Hence the mechanics 400 function to permit adjustments in the height/thickness of the electrophoresis plate 220, gel height/thickness, electrophoresis chamber height, or thickness of the sample.

The gantry 300 is used for sample handling and reagent application. The gantry 300 includes motorized mechanics so that the gantry 300 may be positioned in the XY plane along the X-axis. The gantry position is controlled by the CPU 110 to any location along the X-axis. This is an improvement over existing automatic electrophoresis devices because all of the positioning is controlled by the gantry 300. Thus, electrophoresis plate 220 (shown in FIG. 6) containing the sample does not have to move, thus limiting and consolidating the number of moving parts. The in-situ testing does not require any laboratory technician intervention. In-situ testing is the preferred method of using the invention.

In addition, the ability to move the gantry 300 in the XY plane enables the sample to be placed on the electrophoresis plate 220 by a sample applicator at any location on the X-axis. More importantly, the moveable gantry 300 allows the placing of more than one sample line on the electrophoresis plate 220. These movements are coordinated by using a stepper motor, encoder and a home switch to move the gantry 300 and the CPU 110 to monitor the exact location of the electrophoresis plate 220.

For example, during an typical test, the CPU 110 directs the gantry 300 to draw the sample from a sample tray through pipettes. The samples are transferred from a row of wells on the sample tray to the corresponding wells on the electrophoresis plate 220. The gantry 300 delivers the samples to the electrophoresis plate 220 in an electrophoresis chamber 210 (see FIG. 6) on separation unit 200, returns to the sample tray, then the pipettes are cleaned. The CPU 110 directs the gantry movement so that reagent is delivered to the electrophoresis plate 220 on the separation unit 200, and then the gantry 300 is moved or returned to an initial position near the sample tray to provide clearance for the fluorescent scanner 500. The pipettes are used to draw and deliver a known volume of the sample from the sample tray to the separation unit 200. Various pipettes may be used including bulb pipettes or graduated pipettes. Constant or variable volumes may be transferred. Depending upon the specific test, blade-type applicators rather than pipettes may be used to deliver the sample onto the gel electrophoresis plate 220.

More specifically, in the preferred embodiment, each pipette includes a plunger and a corresponding barrel. The barrel is a column which holds the sample and the plunger is a rod which fits tightly into the barrel from the top. When the plunger is moved out of the barrel, the sample is drawn into the barrel. When the plunger is thereafter pushed into the barrel, the sample is expelled out of the barrel. Thus the extent of movement of the plunger controls the quantity of the sample drawn out of the sample tray or delivered for testing. Conventional motors and encoders are used to move and control the extent of movement of the plungers. The ability to precisely control the movement of the plungers thus permits precise control over the volume of sample. The motors and encoders are controlled by software. The encoders can pulse light or electricity to precisely track the location of each plunger. With this feature the system can vary the quantity of sample placed on the electrophoresis plate 220. By using encoders and motors on the barrels, the system is able to adjust the height at which the samples are deposited. This allows for variations in electrophoresis plate thickness and the like.

In an alternative embodiment, the electrophoresis chamber 210 or the electrophoresis plate 220 can move along the X direction. These embodiments, like the preferred embodiment, allow the sample to be placed anywhere in the XY plane.

The separation unit 200 includes the electrophoresis chamber 210, in which an the electrophoresis plate 220 is placed, and a sample tray. The electrophoresis plate 220 is plastic, preferably a MYLAR plate or backing, on which a coating of cellulose acetate, agarose, or agar gel is applied. One or more motors and encoders track the movement of the gantry 300, thus allowing the samples to be deposited by the pipettes on the electrophoresis plate 220.

The fluorescent scanner 500, the gantry 300, and the separation unit 200 are all controlled by the CPU 110 and the optics and gantry motion is guided by the supports 510. In FIGS. 1A and 1B, the supports 510 are connected to the back of the separation unit 200 and are used to support the fluorescent scanner 500. Tracks are provided on the supports 510 for assisting in positioning the fluorescent scanner 500 onto the electrophoresis chamber 210.

FIG. 2 shows the CPU 110, which directs the operation of the system. A processor in the separation unit 200 controls the process within that unit. The system also includes a keyboard 150 and a color monitor 140 with a touch screen 160 for the laboratory technician input and data storage to the CPU 110. The output from the CPU 110 controls the separation unit 200, the various motors 180, the fluorescent scanner 500, the printer 130, the monitor 140, and the fan motor 185. More specifically, the CPU 110 receives inputs from the keyboard 150 or from the monitor touch screen 160 and initiates the corresponding functional response. For example, if the laboratory technician requests a certain type of test, the CPU 110 initiates the preprogrammed process associated with that test.

Figure 3:
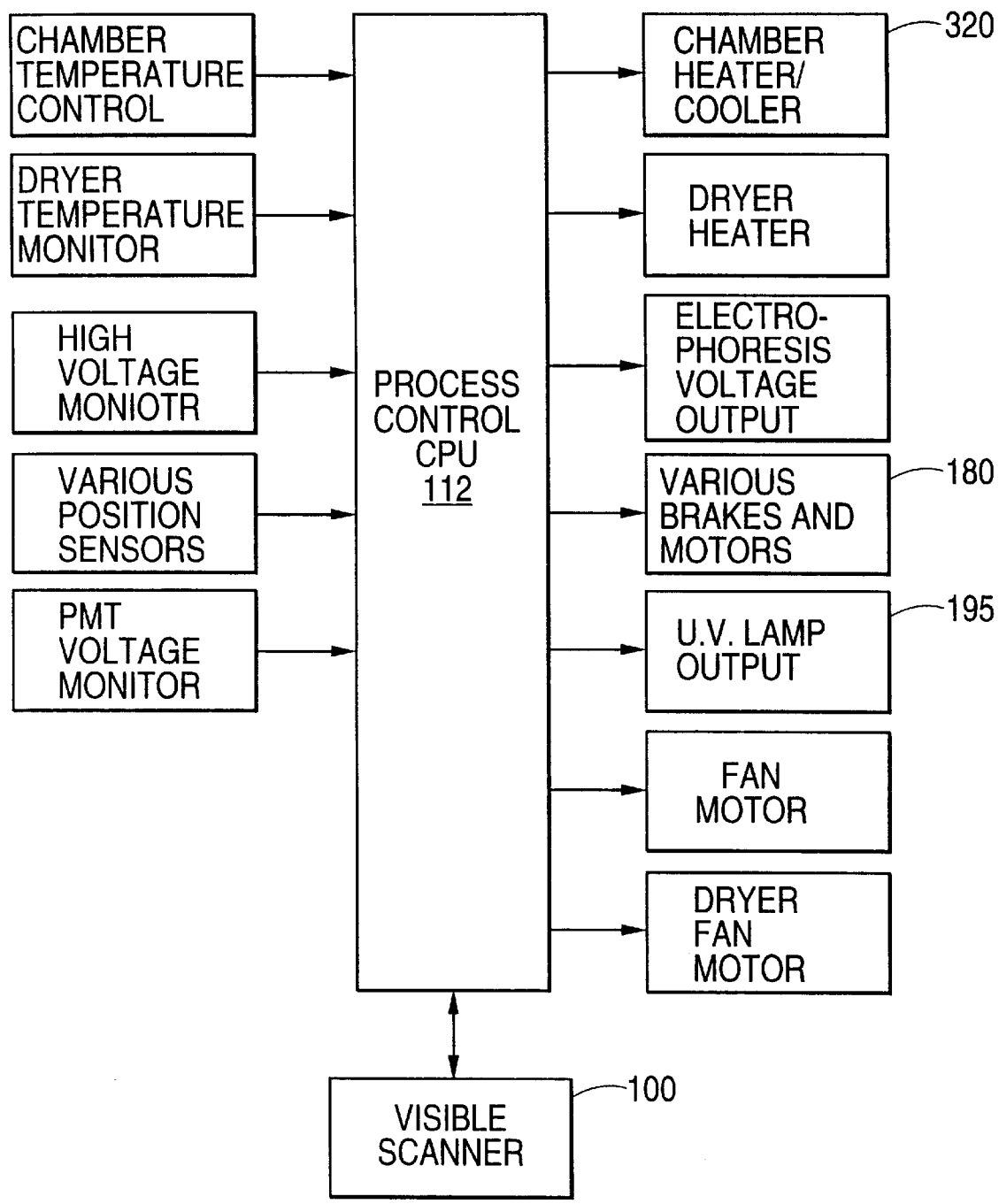
FIG. 3 is a block diagram of the separation unit CPU, also known as the process control CPU.

FIG. 3 shows a process control CPU 112 in the separation unit 200. The CPU 112 directs process control within the separation unit 200. The CPU 112 receives continuously monitored information associated with the status of the system, as opposed to the direct input from the laboratory technician. More specifically, the CPU 112 monitors the electrophoresis chamber temperature, the dryer temperature, the voltage and the various position motors. For example, if the temperature in the electrophoresis chamber 210 increases above the desired range the CPU 112 will initiate the cooling process.

FIG. 4 is a top view of the fluorescent scanner 500 including the mechanics 400 for positioning the fluorescent scanner 500, and the fluorescent scanning unit 415, which includes the fluorescent light sources 195, the photomultiplier tube 450, the filter 440, and the collimator 430. The motorized mechanics 400, which may be a stepper motor, positions the fluorescent scanner 500 along the Z-axis. The motorized mechanics 400 is located in the center of the fluorescent scanner 500 at the end where the fluorescent scanner 500 is connected to the support 510. The supports 510 holds the fluorescent scanner 500 above the electrophoresis chamber 210 and has tracks on which the fluorescent scanner 500 rides toward and away from the electrophoresis chamber 210. A bar 610 is positioned on either side of the motorized mechanics 400 within the support 510 to stabilize the scanner 500. The motor 460, and the motor 410, for positioning the fluorescent scanner 500 within the XY plane above the electrophoresis chamber 210 in the separation unit 200 are also located within the fluorescent scanner 500 and encoders in both the X and Y directions to continuously monitor the position of the fluorescent scanner 500 via the CPU 110.

The fluorescent light sources 195 are generally ultra-violet bulbs or tubes extending in the Y direction. One or more bulbs may be used. When viewed in the direction of FIG. 4, which is a top view, the photomultiplier tube 450, filter 440, slits 420 and collimator 430 appear as concentric circles and ovals in the center of the fluorescent scanner 500. From the side view of FIG. 5A, the collimator 430 is shown leading to the filter 440 and photomultiplier 450. The slits 420 appear in the top and the bottom of the collimator 430.

At the bottom of the fluorescent scanner 500 is the chamber lid 401 for the electrophoresis chamber 210 in the separation unit 200. The chamber lid 401 creates a light seal over the electrophoresis chamber 210 so that the collimator 430 is not exposed to any outside light. In addition, FIG. 5A illustrates two microswitches 435 located on each side of the chamber lid 401. The chamber lid 401 has a total of four microswitches 435 (two of which are not shown in FIG. 5A). The microswitches 435 are a safety device which stops the fluorescent scanner's descent in the Z-direction if there is any contact during movement. Upward pressure on the chamber lid 401 triggers the microswitches 435 and shuts down the stepper motor 400 moving the fluorescent scanner 500 in the Z-direction.

Figure 6:
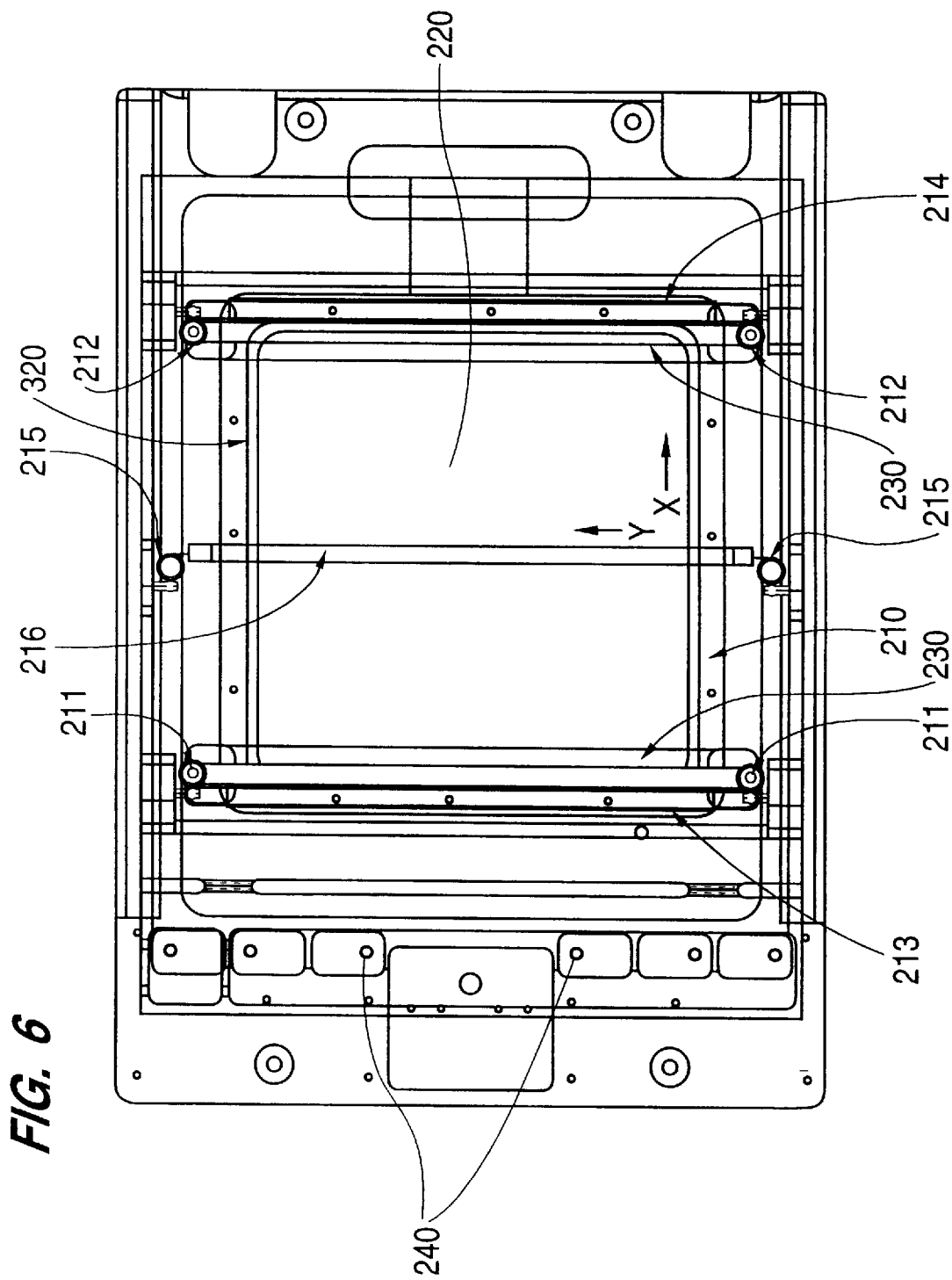
FIG. 6 is a top view of the electrophoresis chamber in the separation unit.

Referring to FIG. 6, the preferred electrophoresis chamber 210 contains a base 205 for resting the electrophoresis plate 220, magnetic switchable electrode posts 211, 212, and 215, two or more parallel electrodes 213, 214, and 216, and one or more glass spreader bars 230. The electrodes 213, 214, and 216 may be attached to the vertically extending electrode posts 211, 212, and 215, with the electrodes 213, 214, and 216, making contact with the electrophoresis plate 220. The spreader bars 230 are located in the vicinity of the electrophoresis plate 220 for spreading reagents and the like. The laboratory technician initially deposits the blood, or any sample, in the sample tray.

Figure 5B:
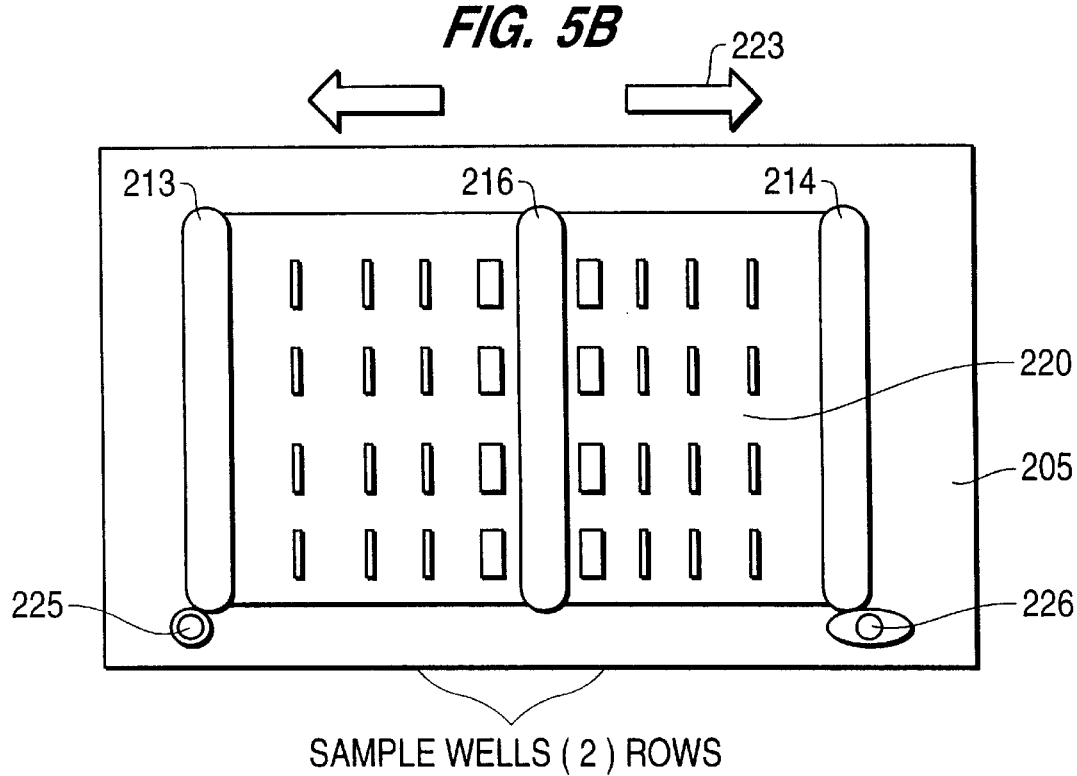
FIGS. 5B and 5C shows a double zone configuration of the electrophoresis chamber.
Figure 5C:
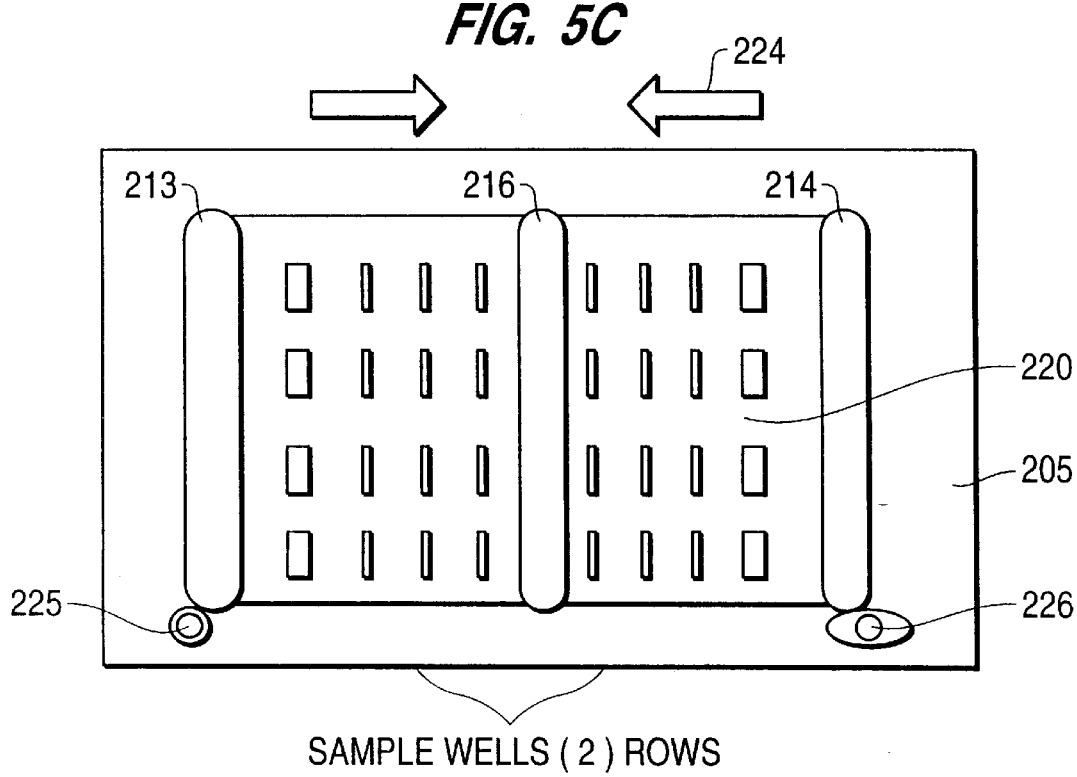
Figure 5D:
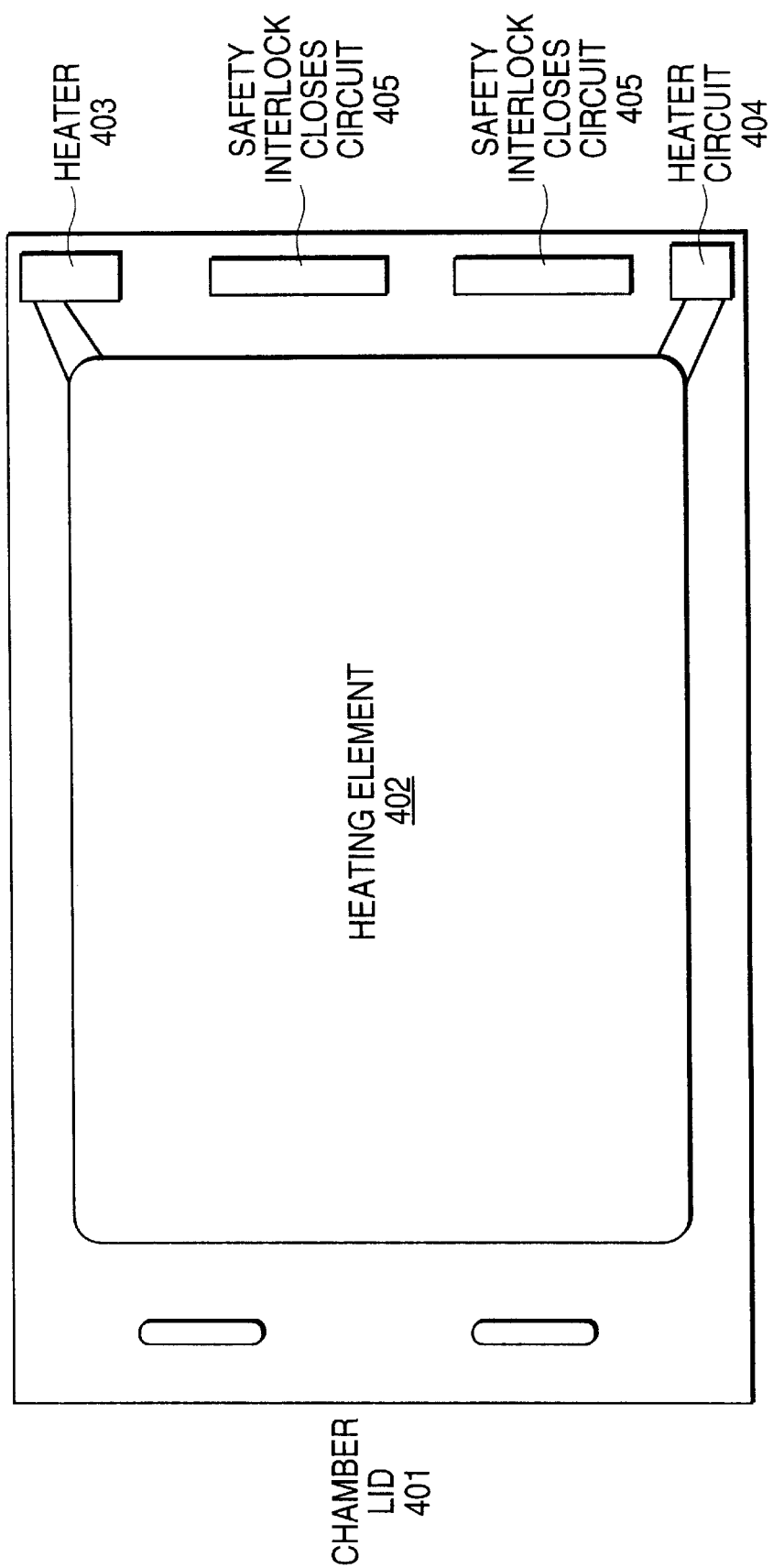
FIG. 5D is the lid to the electrophoresis chamber.

Referring to FIG. 5D, an optional heater 403, heating element 402, and heater circuit 404 on the chamber lid 401 aids in controlling the temperature of the electrophoresis chamber 210. Advantages of a heated chamber lid are the maintaining of a homogenous environment for the electrophoresis plate 220. The chamber lid 401 also has a safety interlock 405 feature. Regardless of whether the chamber lid 401 is heated, the chamber lid 401 contains two contacts or tabs (not shown), which must complete the safety interlock 405 with four corresponding leads (not shown) fixed onto the edges of the electrophoresis chamber 210. Each tab bridges or contacts two leads.

Returning to FIG. 6, the electrophoresis chamber 210 includes a thermo-electric heating/cooling device 320 beneath the electrophoresis plate 220. This thermo-electric heating/cooling device 320 can take a variety of forms including a heat sink with fins. The preferred embodiment uses a Peltier cooling circuit to cool the electrophoresis plate 220 during electrophoresis and during fluorescent scanning. This is advantageous because the fluorescent activity during electrophoresis increases at lower temperatures. Thus, with the thermo-electric heating/cooling device 320, the electrophoresis plate 220 is cooled and bombarded with ultra-violet light simultaneously, to lower the temperature of the electrophoresis plate 220 and thus increase fluorescent activity.

The of electrode posts 211, 212, and 215 are preferably constructed of a permanently magnetized material such as iron, and are adapted to conduct electrophoresis current. The electrode 213 is disposed at one longitudinal end of the electrophoresis chamber 210 and the electrode 214 is disposed at the other longitudinal end of the electrophoresis chamber 210. The electrode 216 is disposed at the midpoint of the electrophoresis chamber 210. Thus, when the electrodes 213, and 214 and the middle electrode 216 are disposed as illustrated in FIG. 6, they are maintained in contact with electrode posts 211, 212 and 215 by the magnetic force between the posts and the ferro-magnetic material of the bar. The spreader bars 230 have steel end tips, or caps, that are also used to keep the spreader bars 230 in contact with the magnetic electrode posts 211, 212, and 215. A left hand positioning peg 208 and a right hand positioning peg 209 ensure that the electrophoresis plate 220 is precisely aligned in the electrophoresis chamber 210.

Referring next to FIGS. 5B and 5C, the electrophoresis chamber 210 may be divided into two smaller chambers when the center electrode 216 is used or installed, and the electrophoresis plates 220 is identified as a 'double zone plates'. In a double zone electrophoresis plate, there are two rows of sample wells 221 and 222. Also shown in FIGS. 5B and 5C are electrophoresis plate alignment pins 225 and 226 that are used to ensure the electrophoresis plate 220 is precisely aligned in the electrophoresis chamber 210. The laboratory technician can select the desired polarity depending on the desired direction of separation. FIG. 5B represents the two outer electrodes 213, 214 being established as anodes with the middle electrode 216 being established as the cathode. The arrows 223 shown the direction of movement of the proteins, for example, in response to the polarity established for the electrodes 213, 214 and 216. FIG. 5C illustrates the opposite polarity, i.e., the outer two electrodes 213, 214 being cathodes and the inner electrode 216 being the anode. The arrows 224 show the sample flow for this polarity. Selecting the polarity of the electrodes 213, 214, 216 may be done dynamically in software by the system or by the laboratory technician.

To accomplish the 'double zone' electrophoresis plate, reference should be had to FIG. 6 where the electrode posts 215 are located midway between the electrode posts 211 and the electrode posts 212. The electrode posts 215 are designed to accommodate the aforementioned middle electrode 216. The middle electrode 216 allows the electrophoresis chamber 210 to contain two separate electrical zones with a smaller distance between the electrodes. In addition, in an embodiment the electrophoresis chamber 210 contains a glass spreader bar 230 on each side of the middle electrode 216 because adding the middle electrode 216 may prevent one spreader bar 230 from spreading the reagents across the entire electrophoresis plate 220. With two spreader bars 230, if the middle electrode 216 is inserted, there is a spreader bar 230 on each side of the middle electrode 216 to spread both of the smaller chambers, or zones, which have been created. Further, the ability to create two separate zones also allows the laboratory technician to have two electrophoretic fields with opposite polarity. In the present invention, regardless of the number of individual zones, each is controlled by the same CPU 112.

In FIG. 6, the electrode posts 215 are shown further apart than the electrode posts 211, 212. This arrangement allows a spreader 230 to pass between the electrode of posts 215. This alternate embodiment may use a wire as the middle electrode 216, instead of a quarter inch thick carbon rod or ferro-magnetic bar, which still creates the smaller zones, but only requires one spreader bar 230 because the spreader bar 230 can pass over a thin middle wire and spread the reagents throughout both of the smaller zones. The wire must be mounted on the side of the electrode posts 215. Thus, in the preferred embodiment, the laboratory technician can dynamically configure the electrophoresis chamber 210 as a single zone with one anode and one cathode, or two zones with a center electrode and two common outer electrodes.

The spreader bars 230 are designed to spread the reagent across the electrophoresis plate 220, after the reagent is deposited by the gantry 300. The reagent highlights the distinctions created by electrophoresis. Thus, it is important to have the reagent evenly distributed throughout the sampled material for some tests.

Figure 7:
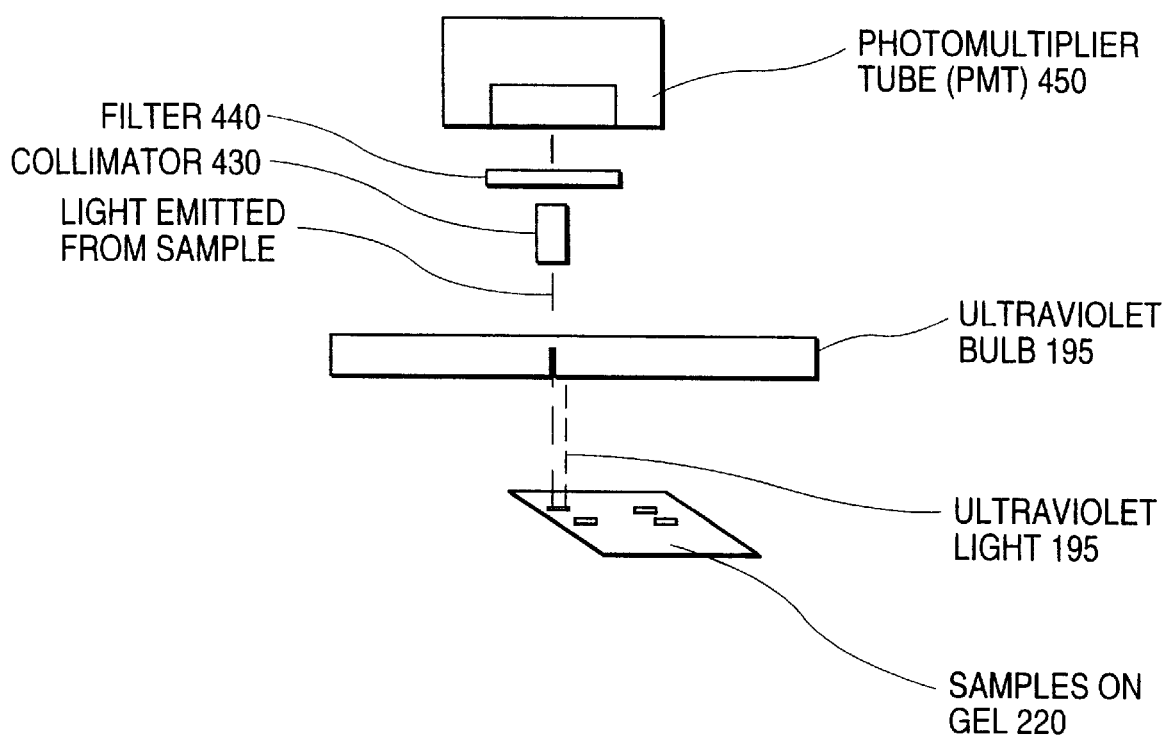
FIG. 7 is a side view of the components of the fluorescent scanner.
Figure 8:
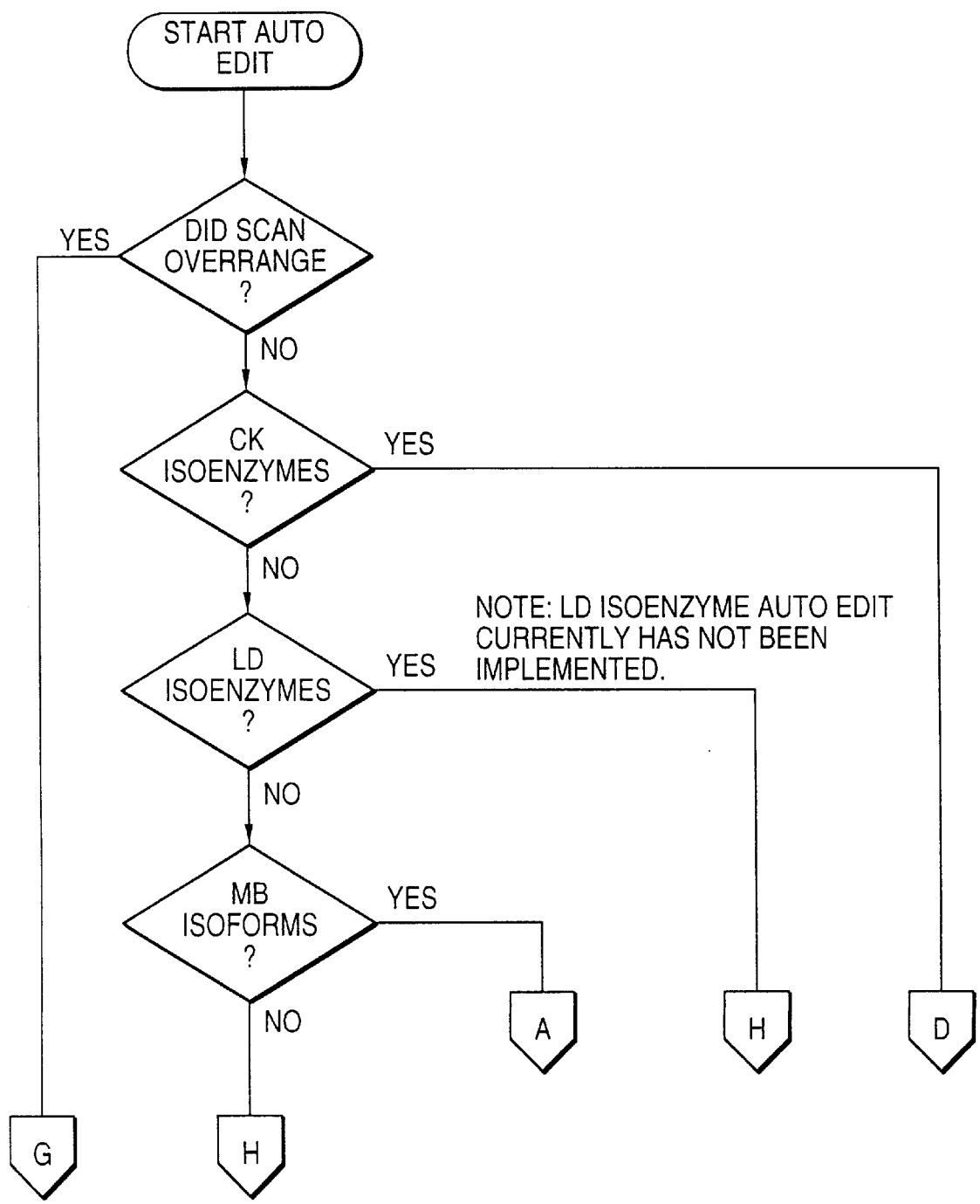
FIGS. 8–14 are a flow diagram of the auto edit process.
Figure 9:
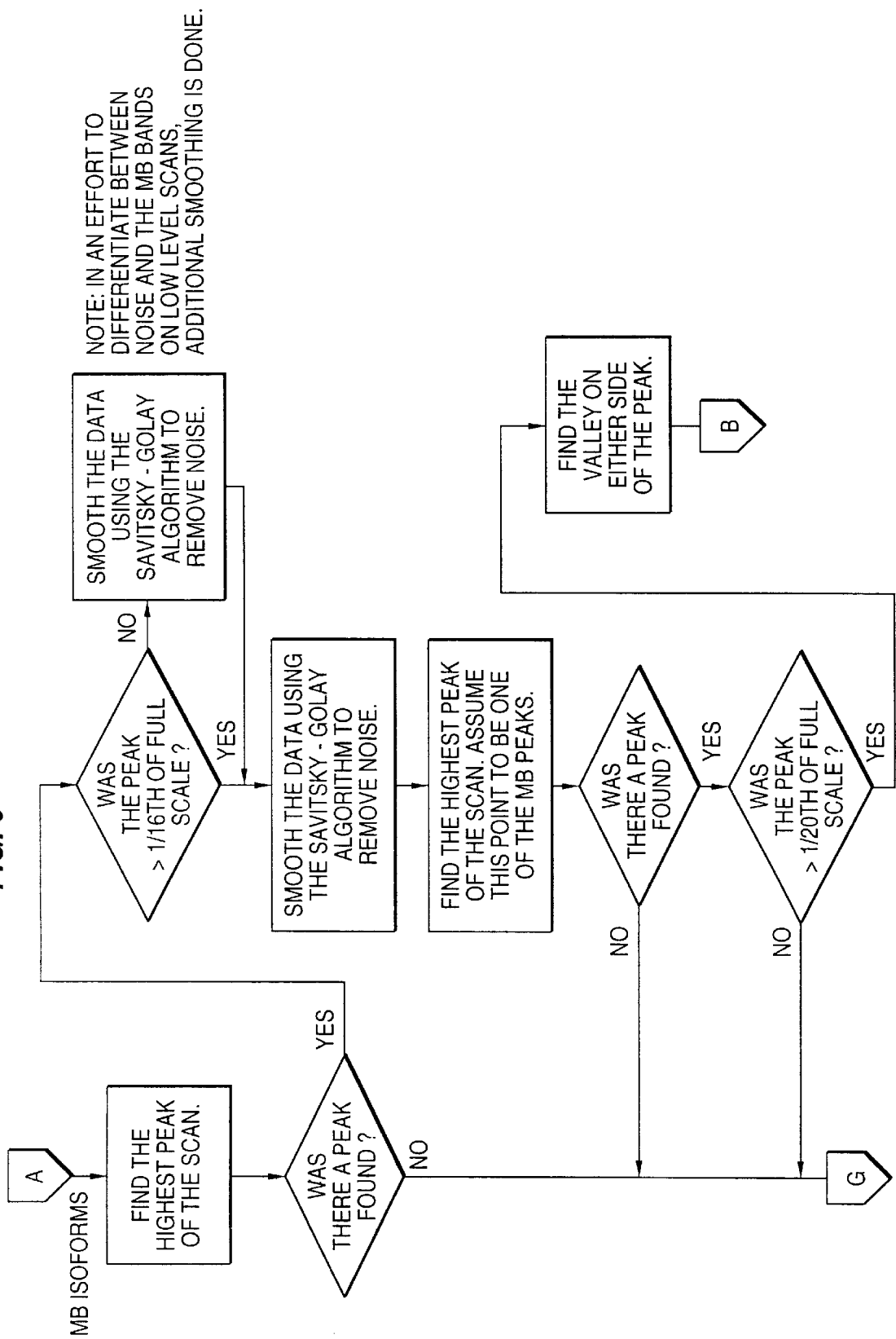
Figure 10:
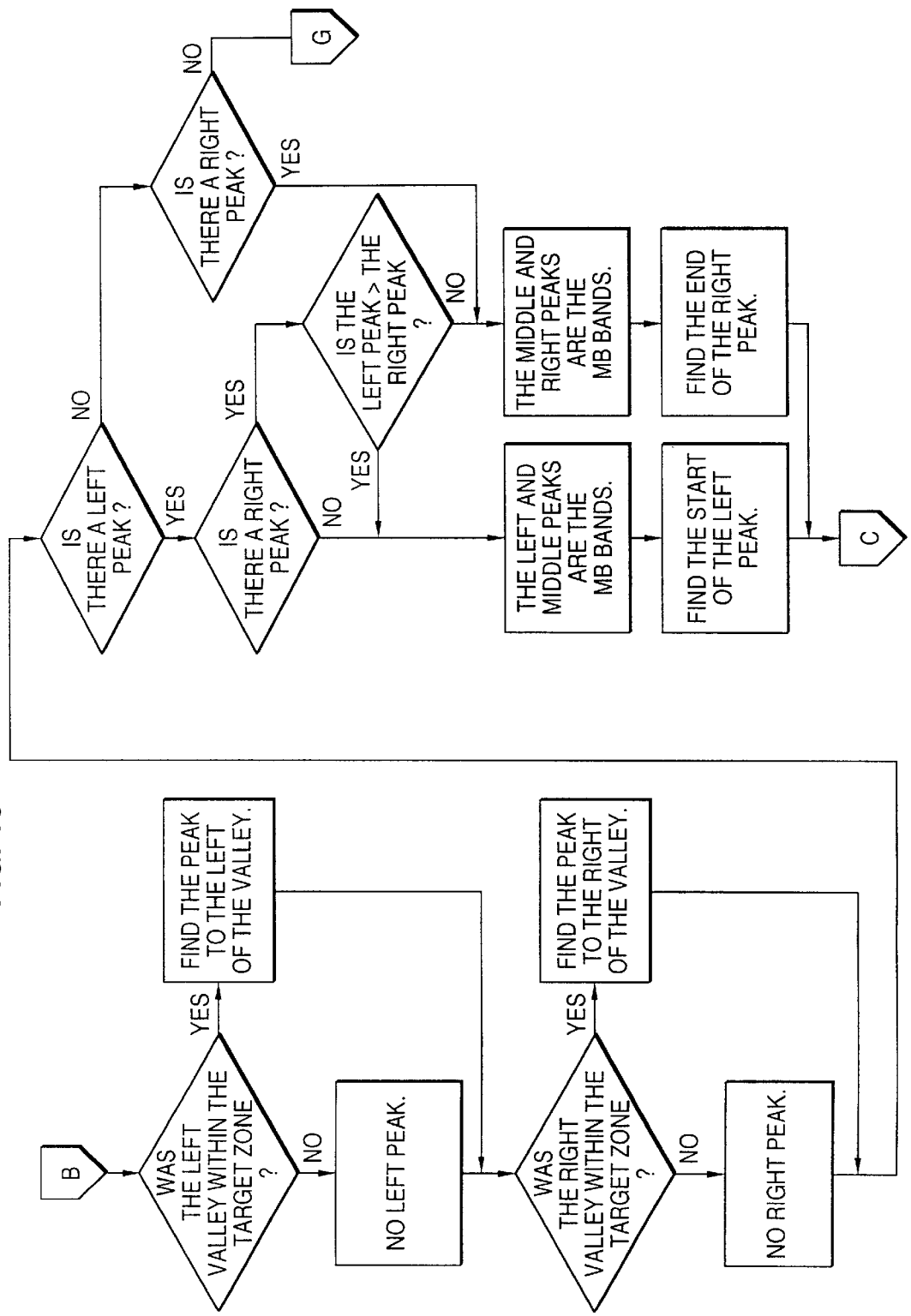
Figure 11:
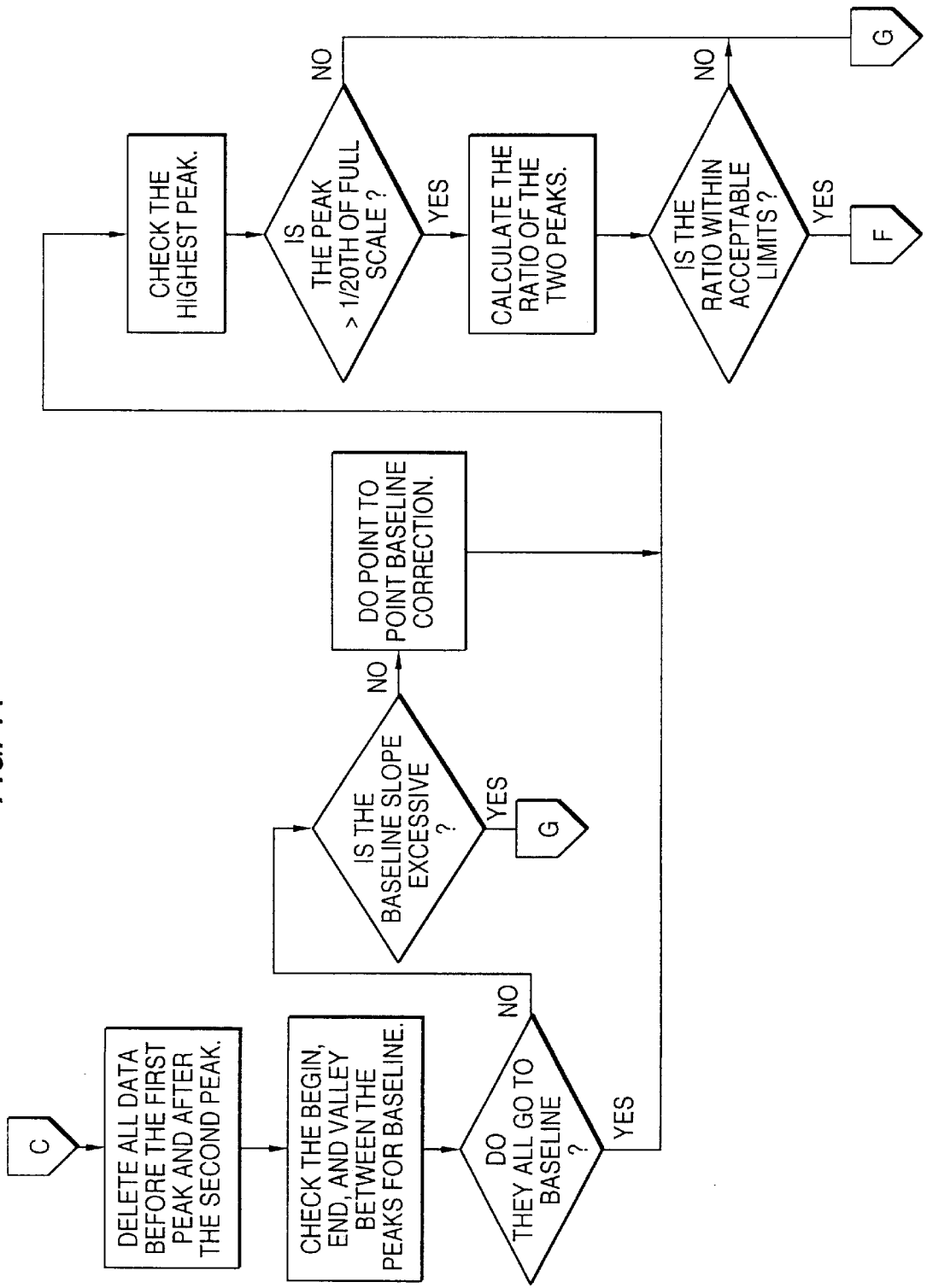
Figure 12:
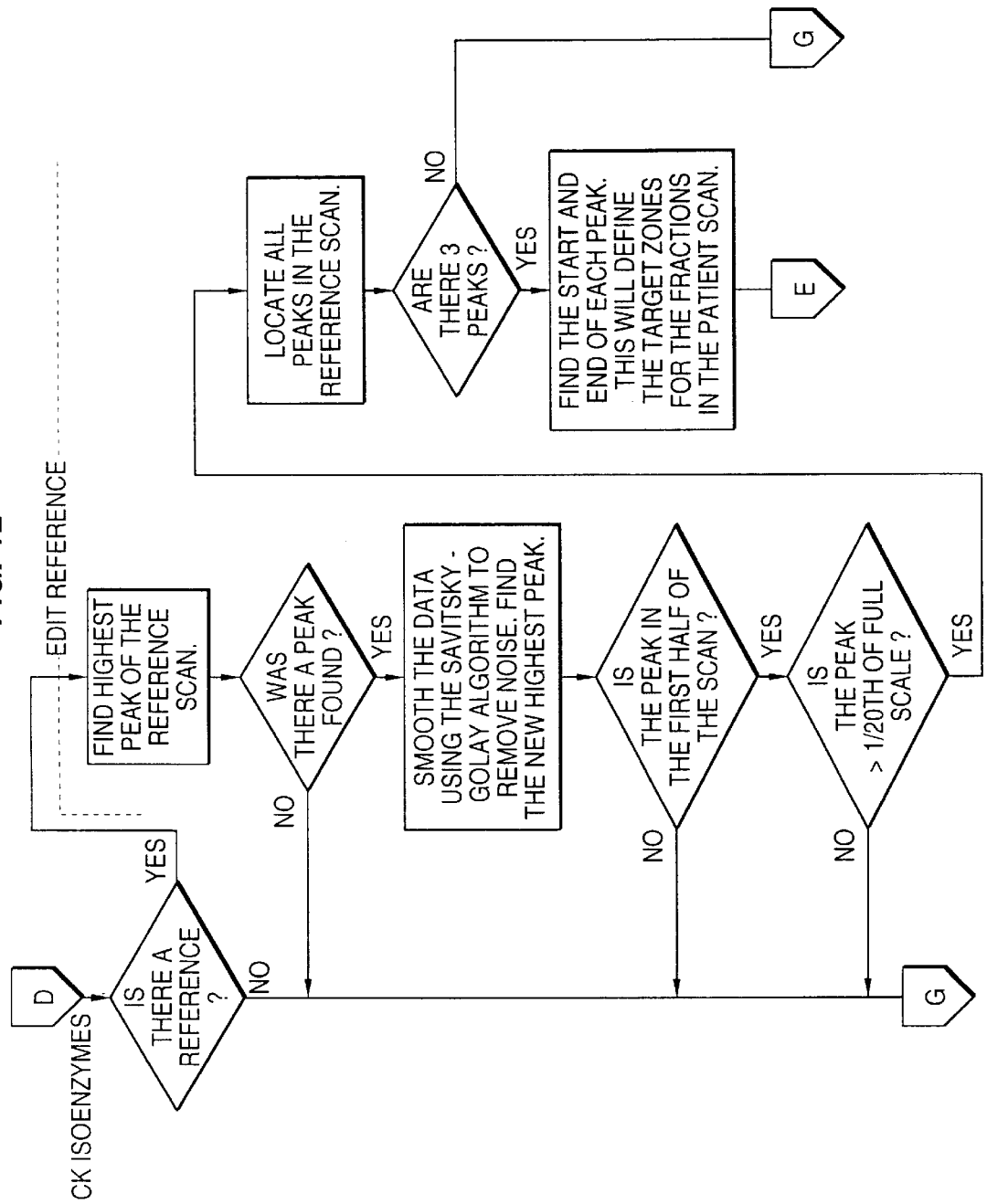
Figure 13:
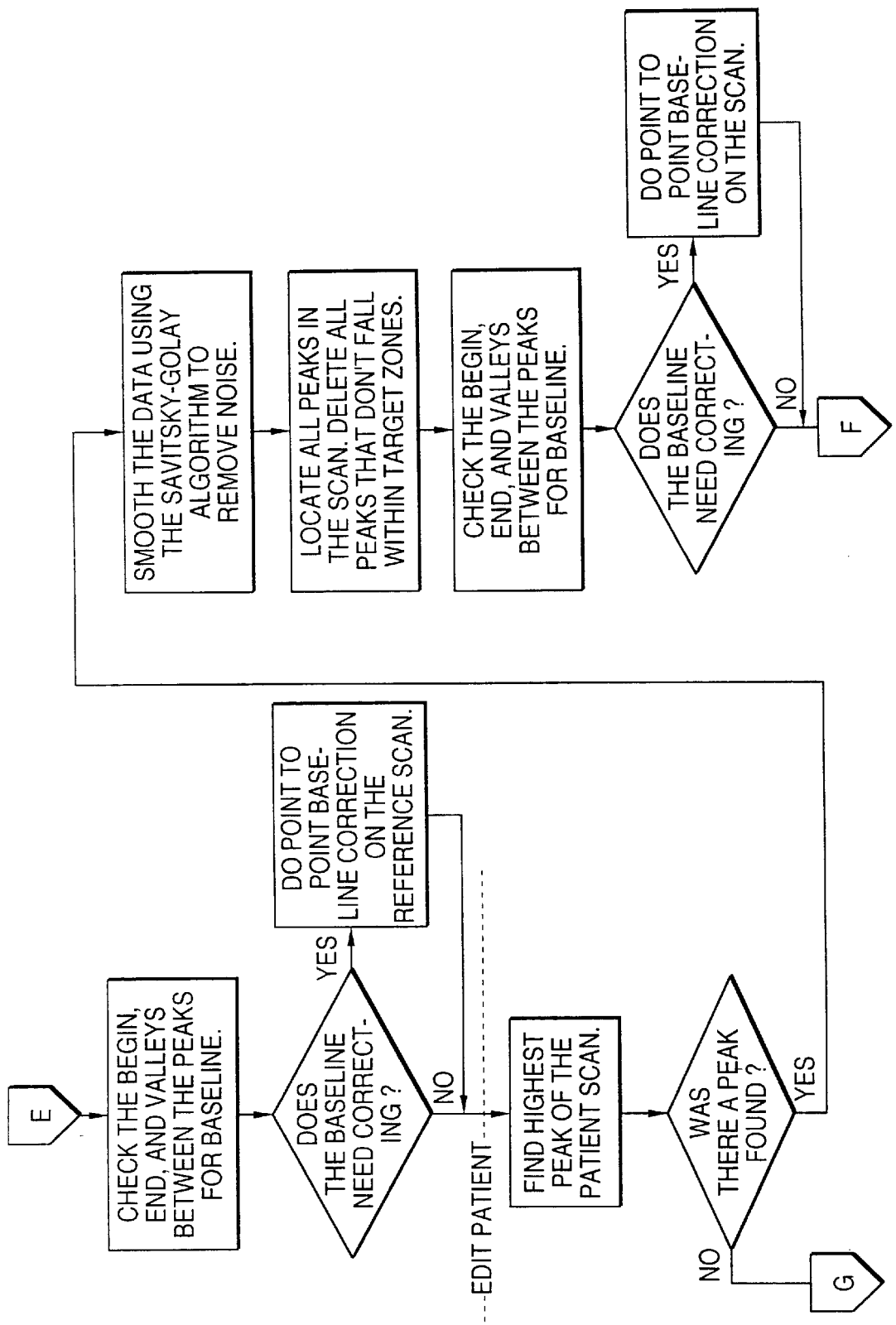
Figure 14:
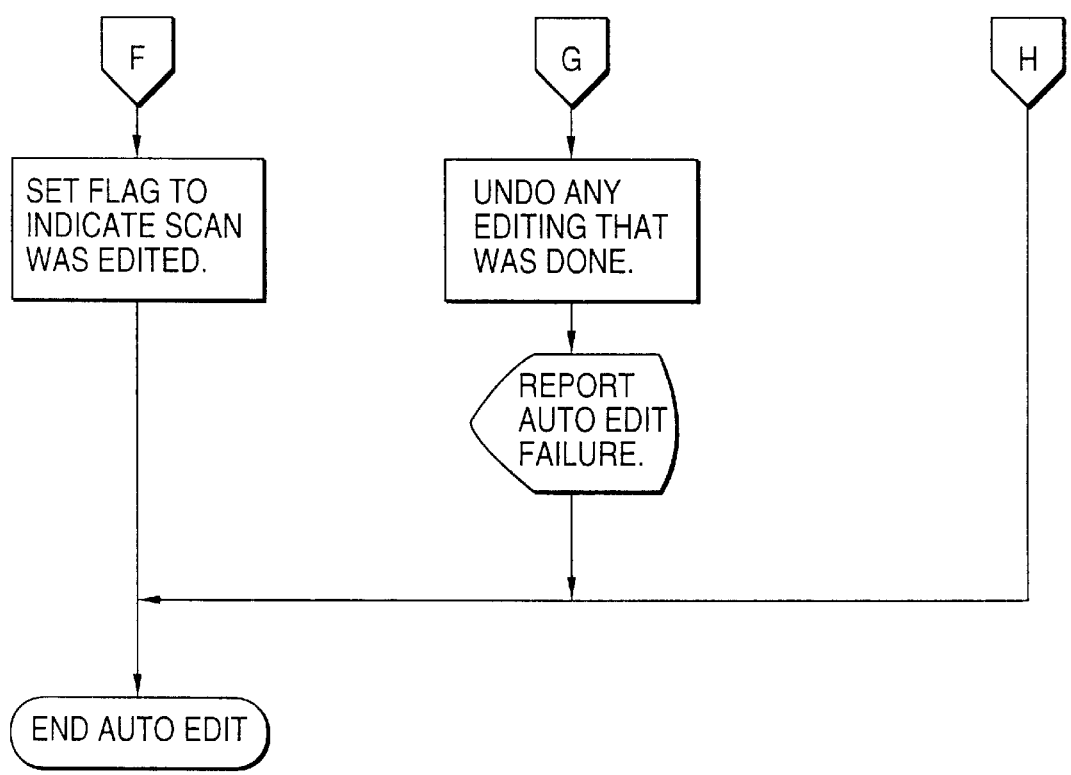

FIG. 7 is a side view of selected components of the fluorescent scanner 500. The samples deposited on the electrophoresis plate 220 are illuminated by the ultraviolet light source 195. The light fluoresced and emitted from the sample goes through the collimator 430 and then through the ultraviolet filter 440, which filters out the ultraviolet light reflected by the sample.

More specifically, when the preferred embodiment is in the fluorescent mode, an ultraviolet light source 195 excites certain compounds in the sample. These compounds result from sample/reagent activity. The excited compounds emit light at a wavelength different from that of the ultraviolet light source 195. The ultraviolet light source 195 is preferred because of safety. Other light sources may be used to radiate samples. Light emitted by the sample reaction product passes through slits 420 in the top and the bottom of the collimator 430 and through ultra-violet filter 440. This results in a high resolution image and permits only light emitted from the sample to reach the photomultiplier tube 450. The fluorescent scanner 500 is lowered over the electrophoresis chamber 210 blocking out other light. The CPU 110 directs the operation of the optics X and Y motors to position the fluorescent scanning unit 415 over the samples and move the fluorescent scanning unit 415 relative to the samples.

The photomultiplier tube 450 generates an output signal, such as electrical current, in proportion to the amount of light received. The relationship between the emitted light and the concentration of the fluorescing sample is linear. Since the light emitted by the sample is low intensity, the voltage to the photomultiplier tube 450 is variable and is normally set automatically by the instrument. The photomultiplier tube voltage may be manually increased or decreased by the laboratory technician to allow higher or lower amplification of the signal if necessary. The photomultiplier tube signal is used by the CPU 110 to calculate data points and generate the areas under the resultant curves for the peaks in the pattern.

FIGS. 8–14 are flow diagrams of the auto edit process. These flow diagrams are self-explanatory.

Using the foregoing embodiments, methods and processes, the automatic electrophoresis apparatus with visible scanning and in situ fluorescent scanning allows the system to maximize functionality, performance, and safety. It will be clear to those in the art that many and varied modifications can be made to the preferred embodiment shown and described. Various changes and modifications are intended to be within the scope of the appended claims.

What is claimed:

1. An apparatus for electrophoresing samples and for scanning the electrophoresed samples, comprising:

an electrophoresis chamber for receiving an electrophoresis plate and samples to be electrophoresed; and a fluorescent scanner operable in the fluorescent scanning mode for scanning the electrophoresed samples which fluoresce when irradiated with light and for receiving the fluoresced light emitted from the sample in response to the irradiated light wherein the fluorescent scanner, comprises:

a fluorescent scanning unit, an X-direction motor coupled to the fluorescent scanning unit, and a Y-direction motor coupled to the fluorescent scanning unit, wherein the X-direction motor and the Y-direction motor operate to position the fluorescent scanning unit relative to the electrophoresis plate, the fluorescent scanning unit receiving the fluorescent light emitted from the electrophoresed samples.

2. The apparatus of claim 1, further including:

a visible scanner operable in the visible scanning mode for scanning the electrophoresed samples and for receiving the visible light;

a central processing unit, connected to the fluorescent scanner and the visible scanner for selecting the mode of scanning, for controlling the operation of the selected scanner, and for providing an output of the result of the scanning;

a gantry for receiving samples, and for delivering samples to the electrophoresis chamber, said central processing unit further connected to and controlling the movement of the gantry.

3. The apparatus of claim 2 wherein the gantry delivers the sample to any position along the x axis of the electrophoresis chamber.

4. The apparatus of claim 2, wherein the gantry delivers samples of more than one volume.

5. The apparatus of claim 1, wherein the fluorescent scanning occurs in situ.

6. The apparatus of claim 2, wherein the gantry delivers samples from different locations on the Z-axis.

7. The apparatus of claim 1, wherein the electrophoresis chamber contains multiple electrodes and more than one electrophoresis zone.

8. The apparatus of claim 7, wherein the electrophoresis chamber contains two electrophoresis zones, a plurality of electrodes, and a spreader bar for spreading reagents, the spreader bar operable to move over at least one electrode.

9. The apparatus of claim 1 wherein the electrophoresed sample is manually moved to the visible scanner.

10. The apparatus of claim 2, wherein the gantry moves along the X-axis.

11. The apparatus of claim 2, wherein an electrophoresis plate is positioned in the electrophoresis chamber, and wherein said gantry applies the sample to the electrophoresis plate and the reagents to the electrophoresis plate.

12. The apparatus of claim 1, wherein the fluorescent scanning unit includes a source of light positioned to irradiate the electrophoresed samples and a detector for receiving the light emitted from the irradiated electrophoresed samples.

13. The apparatus of claim 1, wherein the visible scanner includes a source of light positioned to be directed on the electrophoresed sample.

14. The apparatus of claim 1, further including means for cooling the electrophoresis chamber and means for simultaneously irradiating the samples.

15. An apparatus for electrophoresing samples and for scanning the electrophoresed samples, comprising:

an electrophoresis chamber for receiving an electrophoresis plate and samples to be electrophoresed;

a photomultiplier operable in the fluorescent scanning mode for receiving fluoresced light from an electrophoresed sample;

an X-direction motor coupled to the photomultiplier;

a Y-direction motor coupled to the photomultiplier;

a visible scanner that receives visible light from the electrophoresed sample; and a central processing unit, for selecting the mode of scanning and for providing an output of the result of the scanning, wherein the X- and Y-direction motors operate to scan the photomultiplier over the electrophoresed sample.

16. An apparatus for electrophoresing samples, comprising:

an optical unit comprising:

a first support with mounted tracks for movement of the optical unit in the x and y directions;

a fluorescent scanner for scanning the samples, comprising:

an ultraviolet light source for irradiating the samples;

a collimator for collimating light emitted from the samples;

a photomultiplier tube for detecting light emitted from the samples; and motors for moving the optical unit along the tracks mounted on the first support;

an electrophoresis plate for holding the samples during electrophoresis and scanning, comprising;

a plastic backing; and a gel on the plastic backing; an electrophoresis chamber for the electrophoresis plate comprising:

a base to support the electrophoresis plate;

means for heating the electrophoresis chamber;

means for cooling the electrophoresis chamber;

a cover for the electrophoresis chamber;

at least two parallel electrodes;

at least one bar for spreading reagents on the gel;

a gantry for receiving the samples, delivering the samples to the gel, self-cleaning and delivering reagents to the gel, comprising:

a motor to position the gantry along the X-axis;

at least one pipette for delivery of liquid to the gel;

a second support, connecting the fluorescent scanner, electrophoresis chamber and gantry, comprising:

Z-direction tracks for the fluorescent scanner;

X-direction tracks for the gantry;

a loading tray for the samples;

and a central processing unit, connected to the fluorescent scanner and the gantry, for controlling the operation of the electrophoresis and scanning.

17. The apparatus of claim 16, further including:

a visible scanner comprising:

a light source; and said central processing unit connected to the visible scanner for selecting either the visible scanner or the fluorescent scanner for scanning densitometry of the electrophoresed sample.

* * * * *